(12) United States Patent
Radivojevic et al.

(10) Patent No.: US 11,841,990 B2
(45) Date of Patent: Dec. 12, 2023

(54) HAPTIC FEEDBACK (71) Applicant: Nokia Technologies Oy, Espoo (FI)

(72) Inventors: Zoran Radivojevic, Cambridge (GB); David Bitauld, Massy (FR); Ian Davis, County Wicklow (IE)

(73) Assignee: Nokia Technologies Oy, Espoo (FI)

(*) Notice: Subject to any disclaimer, the term of this patent is extended or adjusted under 35 U.S.C. 154(b) by 114 days.

(21) Appl. No.: 17/434,216

(22) PCT Filed: Mar. 11, 2020

(86) PCT No.: PCT/EP2020/056444
§ 371 (c)(1),
(2) Date: Aug. 26, 2021

(87) PCT Pub. No.: WO2020/200673
PCT Pub. Date: Oct. 8, 2020

(65) Prior Publication Data
US 2022/0187917 A1  Jun. 16, 2022

(30) Foreign Application Priority Data

Mar. 29, 2019 (EP) .................................... 19166199

(51) Int. Cl.
*G06F 3/01* (2006.01)
*A63B 71/06* (2006.01)
*G08B 6/00* (2006.01)

(52) U.S. Cl.
CPC .......... *G06F 3/016* (2013.01); *A63B 71/0619* (2013.01); *G06F 3/011* (2013.01);
(Continued)

(58) Field of Classification Search
CPC ..... G06F 3/016; G06F 3/011; A63B 71/0619; A63B 2071/0655; A63B 2230/62;
(Continued)

(56) References Cited

U.S. PATENT DOCUMENTS 10,642,368 B2* 5/2020 Chen ....................... G01S 11/14
2006/0022833 A1  2/2006 Ferguson et al.
(Continued)

FOREIGN PATENT DOCUMENTS

CN   208112614 U  * 11/2018
EP   2995096 A1    3/2016
(Continued)

OTHER PUBLICATIONS

Office Action received for corresponding European Patent Application No. 19166199.0, dated Feb. 11, 2022, 5 pages.
(Continued)

*Primary Examiner* — Quan Zhen Wang
*Assistant Examiner* — Mancil Littlejohn, Jr.
(74) *Attorney, Agent, or Firm* — Harrington & Smith (57) ABSTRACT

A system for providing haptic feedback to a user, the system comprising a first piezoelectric transducer array comprising multiple piezoelectric transducers, respective ones of which being configured to generate a second signal at a second frequency, and at least one of which being configured to generate a first signal at a first frequency, and a second piezoelectric transducer array comprising multiple piezoelectric transducers, respective ones of which configured to receive the second signal, and at least one of which configured to generate a third signal to initiate generation of the first signal at the said at least one piezoelectric transducer of the first piezoelectric transducer array, the first frequency suitable for providing a haptic feedback signal for a user.

19 Claims, 8 Drawing Sheets

(52) U.S. Cl.
CPC ........ *G08B 6/00* (2013.01); *A63B 2071/0655* (2013.01); *A63B 2230/62* (2013.01)

(58) Field of Classification Search
CPC ......... G08B 6/00; A61B 5/1114; A61B 5/002; G01S 5/30
See application file for complete search history.

(56) References Cited

U.S. PATENT DOCUMENTS

| | | |
|---|---|---|
| 2017/0061817 A1 | 3/2017 | Mettler May |
| 2017/0154505 A1 | 6/2017 | Kim |
| 2018/0028777 A1 | 2/2018 | Cheng |
| 2018/0151035 A1 | 5/2018 | Maalouf et al. |

FOREIGN PATENT DOCUMENTS

| | | | | |
|---|---|---|---|---|
| EP | 2995096 B1 * | 12/2017 | ............. | G01S 15/36 |
| GB | 2513884 A | 11/2014 | | |
| WO | 2014/114967 A1 | 7/2014 | | |
| WO | WO-2014114967 A1 * | 7/2014 | ........... | A61B 5/0024 |
| WO | 2014/181084 A1 | 11/2014 | | |

OTHER PUBLICATIONS

Xu et al., "Configurable, Wearable Sensing and Vibrotactile Feedback System for Real-time Postural Balance and Gait Training: Proof-of-concept", Journal of NeuroEngineering and Rehabilitation, vol. 14, Oct. 2017 pp. 1-10.

Extended European Search Report received for corresponding European Patent Application No. 19166199.0, dated Sep. 16, 2019, 9 pages.

International Search Report and Written Opinion received for corresponding Patent Cooperation Treaty Application No. PCT/EP2020/056444, dated May 25, 2020, 12 pages.

* cited by examiner

HAPTIC FEEDBACK

RELATED APPLICATION

This application was originally filed as a Patent Cooperation Treaty Application No. PCT/EP2020/056444 filed on Mar. 11, 2020, which claims priority to European Application No. 19166199.0, filed on Mar. 29, 2019, the contents of which are hereby incorporated in their entirety.

TECHNICAL FIELD

Aspects relate, in general, to providing haptic feedback, and more particularly to a system and method for providing haptic feedback.

BACKGROUND

Haptic technology can be used to provide contact or non-contact feedback to a user. For example, the application of motions and vibrations to a user can be used in order to recreate the sense of touch, which may be used to communicate with the user in response to some action performed or to be performed for example.

SUMMARY

According to an example, there is provided a system for providing haptic feedback to a user, the system comprising a first piezoelectric transducer array comprising multiple piezoelectric transducers, respective ones of which being configured to generate a second signal at a second frequency, and at least one of which being configured to generate a first signal at a first frequency, and a second piezoelectric transducer array comprising multiple piezoelectric transducers, respective ones of which configured to receive the second signal, and at least one of which configured to generate a third signal to initiate generation of the first signal at the said at least one piezoelectric transducer of the first piezoelectric transducer array, the first frequency suitable for providing a haptic feedback signal for a user. The third signal can be generated at the second frequency. The first piezoelectric transducer array can be provided on or as part of an item of clothing. The first frequency can be a frequency in the range 10-2000 Hz. The second frequency can be a frequency in the range 15-50 kHz. A control module can be provided to receive raw data from respective piezoelectric transducers of the second piezoelectric transducer array, and, using the raw data, generate position data representing the relative position of the multiple piezoelectric transducers of the first piezoelectric transducer array. The control module can map the position data to a predetermined haptic response profile, and generate haptic response data representing the haptic response profile. A selected piezoelectric transducer of the second piezoelectric transducer array can transmit the haptic response data as part of the third signal. The control module can use respective time stamps from the raw data representing the times of transmission of second signals from respective piezoelectric transducers of the second piezoelectric transducer array to determine a time of flight of the second signals. A low energy radio-frequency communication module to receive a data signal from a command transducer of the first piezoelectric transducer array can be provided. The third signal can be generated by the low energy radio-frequency communication module of the command transducer. The command transducer can transmit data to selected ones of the low energy radio-frequency communication modules of the piezoelectric transducers of the first piezoelectric transducer array whereby to cause the corresponding piezoelectric transducers of the first piezoelectric transducer array to generate the first signal.

According to an example, there is provided a method, comprising emitting an ultrasonic signal from a first device, receiving the emitted ultrasonic signal at multiple other devices, comparing respective waveforms of the emitted ultrasonic signal received at the said multiple other devices with a waveform of the emitted ultrasonic signal, determining respective times of arrival of the emitted ultrasonic signal at the multiple other devices, and determining the locations of the multiple other devices. Comparing can include cross-correlating the waveforms of the emitted ultrasonic signal received at the said multiple other devices with the waveform of the emitted ultrasonic signal. The signal can be a chirp.

According to an example, there is provided a non-transitory machine-readable storage medium encoded with instructions executable by a processor for providing haptic feedback to a user, the machine-readable storage medium comprising instructions to determine the relative or absolute positions of respective multiple transducers arranged on the user, compare the determined positions with one or more desired positions for the user, and on the basis of the comparison, generate haptic feedback data to generate a haptic feedback signal for at least one of the said multiple transducers, whereby to provide haptic feedback to the user.

BRIEF DESCRIPTION OF THE DRAWINGS

Embodiments will now be described, by way of example only, with reference to the accompanying drawings, in which.

DESCRIPTION

Example embodiments are described below in sufficient detail to enable those of ordinary skill in the art to embody and implement the systems and processes herein described. It is important to understand that embodiments can be provided in many alternate forms and should not be construed as limited to the examples set forth herein.

Accordingly, while embodiments can be modified in various ways and take on various alternative forms, specific embodiments thereof are shown in the drawings and described in detail below as examples. There is no intent to limit to the particular forms disclosed. On the contrary, all modifications, equivalents, and alternatives falling within the scope of the appended claims should be included. Elements of the example embodiments are consistently denoted by the same reference numerals throughout the drawings and detailed description where appropriate.

The terminology used herein to describe embodiments is not intended to limit the scope. The articles "a," "an," and "the" are singular in that they have a single referent, however the use of the singular form in the present document should not preclude the presence of more than one referent. In other words, elements referred to in the singular can number one or more, unless the context clearly indicates otherwise. It will be further understood that the terms "comprises," "comprising," "includes," and/or "including," when used herein, specify the presence of stated features, items, steps, operations, elements, and/or components, but do not preclude the presence or addition of one or more other features, items, steps, operations, elements, components, and/or groups thereof.

Unless otherwise defined, all terms (including technical and scientific terms) used herein are to be interpreted as is customary in the art. It will be further understood that terms in common usage should also be interpreted as is customary in the relevant art and not in an idealized or overly formal sense unless expressly so defined herein.

For numerous reasons, it may prove difficult for individuals to exercise or otherwise move their body in certain ways. For example, due to time constraints or other pressures, individuals may forget to exercise. In another context, individuals may experience difficulty moving their body, or parts thereof, in certain ways, such as when playing or learning to play certain sports, when exercising, gaming, taking part in the performing arts, and so on. That is, certain activities can require an individual to perform certain movements in a specific way, either to gain the optimum benefit or because the activity demands that the individual places their body into a certain pose, posture or position. Without either motivation or the correct experience and/or training, individuals may struggle to do this.

According to an example, there is provided a (user) wearable system which provides a human body movement guidance control system and method. In an example, multiple piezoelectric transducers (vibrators/emitters/receivers) can be distributed on an individual (e.g. on one or more items of clothing, or directly to the user using suitable adhesive or by strapping etc.) and/or the surrounding environment (rooms/walls/callings/cars etc.). At least some of the transducers can operate in a Dual Frequency Mix (DFM) mode of operation targeting two operating bands: a low frequency band (from between 10-2000 Hz, and ideally around 200 Hz), which band being well-suited for haptic feedback, and a higher frequency band, such as one operating at ultrasonic frequencies (from around 15-50 kHz, and ideally around 20 kHz), which higher band being suitable for enabling transducer localisation, as will be described below in more detail.

In an example, the relative position of transducers that are disposed on an individual can be determined by calculating distance information (e.g. using time of flight (TOF), time of delay of arrival (TDOA) and/or angle of arrival (AOA) measurements) from signals transmitted and received between transducers in the ultrasonic band. This distance data can then be used to calculate the relative positions of the transducers using, for example, trilateration, triangulation and/or multilateration.

According to an example, DFM enables tandem operation of the same physical module (e.g. a transducer fabricated from piezoelectric material) to work as a haptic vibrator-actuator and/or ultrasonic emitter/receiver sequentially. The low frequency component mentioned above enables well-perceived haptic skin stimulations (via energy transferred to human body) while an ultrasonic frequency enables TOF distance measurement in the real time.

Human skin is not sensitive to ultrasonic frequencies, which therefore makes the DFM technique suitable for the real time TOF measurements with no risks of interfering with haptic feedback. Accordingly, the same piezoelectric transducer can be used for dual functionality; i.e. providing a system with haptic feedback guided by TOF measurements (i.e. distances between transducers) by using the same modules.

In an example, distribution of transducers on an individual (e.g. by way of distribution on a garment of clothing to be worn by that individual) can be provided in such a way that TOF measurements are obtained as relative distances between the transducers. Accordingly, transducers placed on an individual can be used to determine posture information for the individual by exploiting localisation techniques. More particularly, in an example, relative positions of body parts (limbs, hands, legs, head, stomach, fingers, torso and so on), and overall body shapes can be tracked/monitored in real time. That is, positions of transducers relative to one another can provide an indication of body position/posture.

According to an example, an internal clock for TOF measurements and synchronisation between multiple transducers can be transmitted between transducers using embedded Bluetooth signal modules. The modules can include a clock in order to generate a clock signal for transmission. When the clock signal between transducers is synchronised, and by exploiting triangulation for example, a system according to an example can be used to enable determination of the positions of the limbs, legs and other postures.

In an example, the position of transducers relative to one another can be optimised to ensure that dilution of precision is minimised, which is a source of uncertainty in localisation algorithms related to the relative positions of sources and receivers. Since, in an example, each transducer can act as both source and receiver, there is also redundancy in the localisation system (more distance information than is necessary to implement triangulation, for example). This redundancy can help ensure robustness in the face of measurement errors e.g. due to multipath propagation from source to receiver.

Once a position of a body part or a posture of an individual is determined, the system can issue haptic feedback. For example, in accordance with pre-determined patterns (patterns can be static and/or dynamic modalities i.e. time dependant and in accordance with previously achieved moving patterns for example). In this way, real-time haptic feedback can provide guidance of dynamic motion of a person wishing to achieve some of moving patterns.

For example, when a certain posture or position of a body part or body as a whole is determined by way of the spatial location of limbs/legs/torso etc. relative to one another, haptic feedback can be issued to the user. In an example, the feedback can be geared towards enabling the user to recognise and learn (via low cognitive effort haptic feedback) how to perform certain movements and what is the right posture for a particular moment for example. This may be used dynamically by providing, in real time, haptic feedback about appropriate movements in, for example, exercising, yoga, ballet, sports or athletic applications and so on. For example, haptic feedback can be provided by one or more transducers that provide a physical recreation of the sense of touch for a user that can prompt them to engage in some predetermined movement or positional adjustment. For example, haptic feedback provided on one transducer of an arm can be a signal to prompt the user in question to move that arm in a particular way/direction and so on. In an example, haptic feedback can persist until the user has moved or changed a position to that desired, or can be transient. Various types of haptic feedback can be provided. For example, a transducer can be configured to vibrate at a selected frequency, with a selected intensity, periodically and so on in order to provide different haptic feedback signals that can be used to signify different things or instructions. For example, a periodic haptic feedback signal provided to a user (e.g. every 0.5 s) can be a prompt for the user to move a body part in question upwards. Conversely, a continuous haptic feedback signal provided to a user can be a prompt for the user to move a body part in question downwards. Other alternatives are possible. That is, it will be apparent that various haptic signals can be mapped to various different positional requirements or movement prompts.

In an example, a system as described herein can be used by a single or multiple users. In the latter case, users can be connected by a Bluetooth radio module to exchange the signals and share the same clock time. In multiple user case, the system might guide the second, third, etc. user to mimic movements of the first (guide) one and in accordance with his guidance and lead (like "dance with me" or "please follow my body moments").

Figure 1:
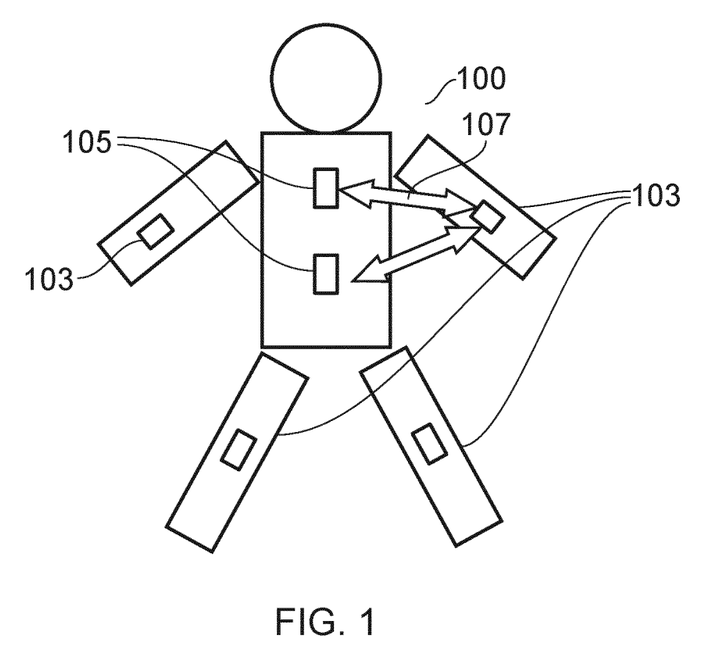
FIG. 1 is a schematic representation of a system, according to an example.

FIG. 1 is a schematic representation of a system, according to an example. In the example of FIG. 1, the system is depicted in situ on a user 100. The user 100 is supplied with the piezo-electric modules (transducers) distributed on the body parts where the measurements and haptic feedback will be provided. In an example, there is provided a first piezo-electric transducer array comprising multiple piezoelectric transducers 103, respective ones of which configured to generate a first signal at a first frequency, which can be a haptic feedback frequency as described above, and a second signal at a second frequency, which can be an ultrasonic frequency as described above. A second piezoelectric transducer array comprising multiple piezoelectric transducers 105 is provided, respective ones of which configured to receive the second signal, and at least one of which is configured to generate a third signal at the second frequency. Although two transducers for the second array are depicted in FIG. 1, it will be appreciated that more can be provided. Transducers of the first and/or second array may be provided on clothing, or directly attached to a user or a combination.

In an example, transducers 103 of the first array can send and receive signals at the second frequency to/from transducers 105 of the second array. This enables time of flight measurements to be determined as the time of flight of a second signal to and/or from a transducer 103 from/to a transducer 105 can be obtained with reference to common clock signal that can be provided to transducers in the first and second arrays. In an example, each transducer in the first and second arrays includes a low energy radio frequency module, such as a Bluetooth low energy (or similar) module (BLE) for example. One of the transducers 105 in the second array can provide central clock information using a communication channel initiated between transducers using the BLE module. That is, in an example, one of the transducers in the second array can provide a clock signal, and other control information, to respective other ones of the transducers in the first and/or second arrays.

In an example, respective second signals can be time stamped with a time of transmission, and/or with a unique identifier that enables the originating transducer to be determined (i.e. each transducer can have a unique identifier associated with it). Accordingly, upon receipt of a time stamped second signal from a transducer of the first array by a transducer of the second array (or vice versa), the time of receipt of a second signal can be used to calculate the time of flight or time of arrival of that signal, thereby enabling, for example, the distance of the transducer of the first array, as identified by the embedded identifier, from a receiving transducer of the second array to be determined. Since the same signal can be received by multiple transducers of the second array, a set of time of flight data can be generated that enables the position of the originating transducer (of the first array) to be determined using one of the techniques noted above (tri- or multilateration etc.). In this connection, in an example, the second array can comprise at least three transducers. In an example, in order to find the position of a transducer in n dimensions (e.g. n=3), at least n+1 time of arrival signals must be measured.

Figure 2:
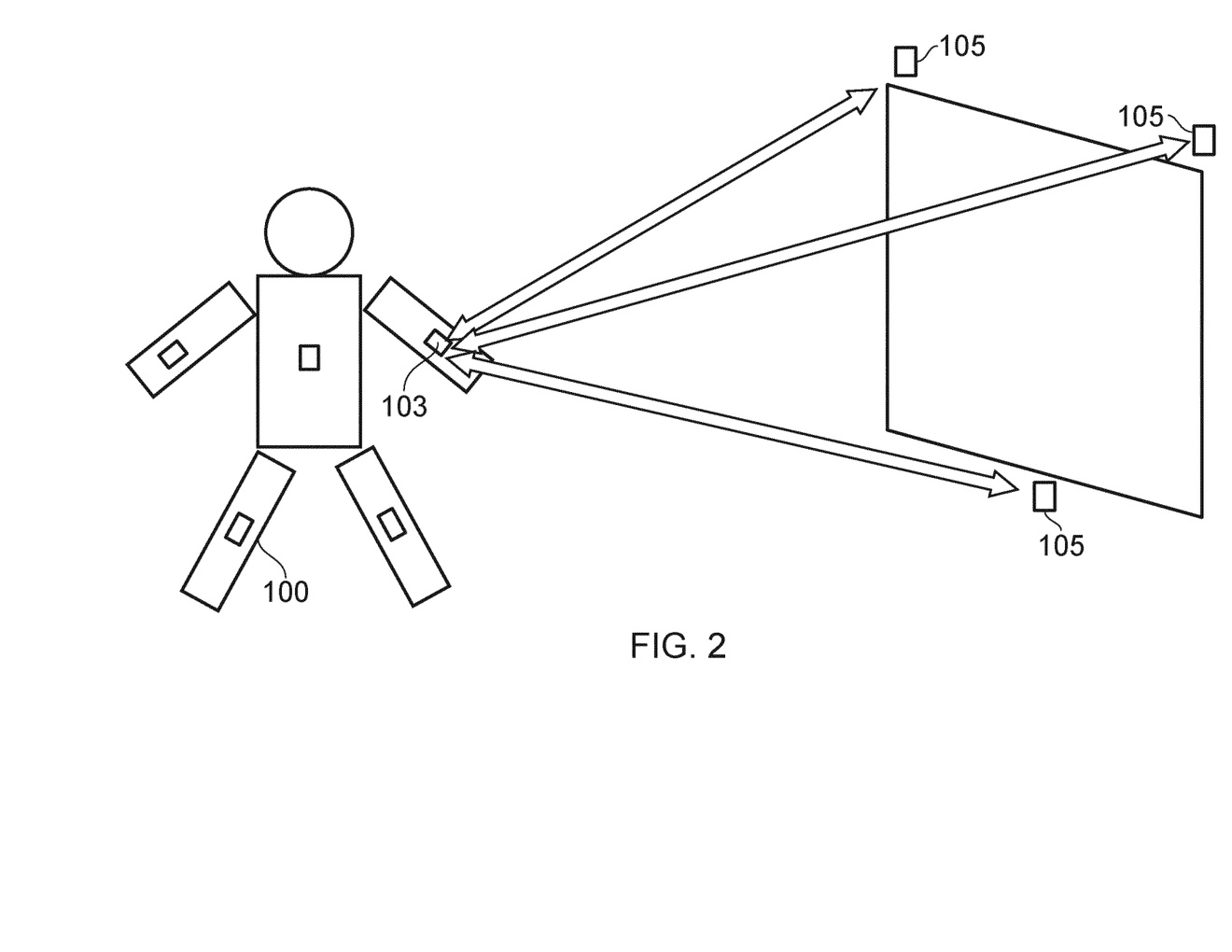
FIG. 2 is a schematic representation of a system according to an example.

FIG. 2 is a schematic representation of a system according to an example. In the example of FIG. 2, the distribution of transducers of the second array can be extended out to the surrounding environment where some or all of the transducers of the second array, used for triangularisation and TOF generation, can be located. FIG. 2 depicts all such transducers extended out, although one or more may still be provided in situ on user 100. Transducers 103 (five in the example of FIGS. 1 and 2) that are used to provide haptic feedback to user 100 remain on the user body. This can therefore minimise the number of the modules on the user and simplify the hardware on the body.

Figure 3:
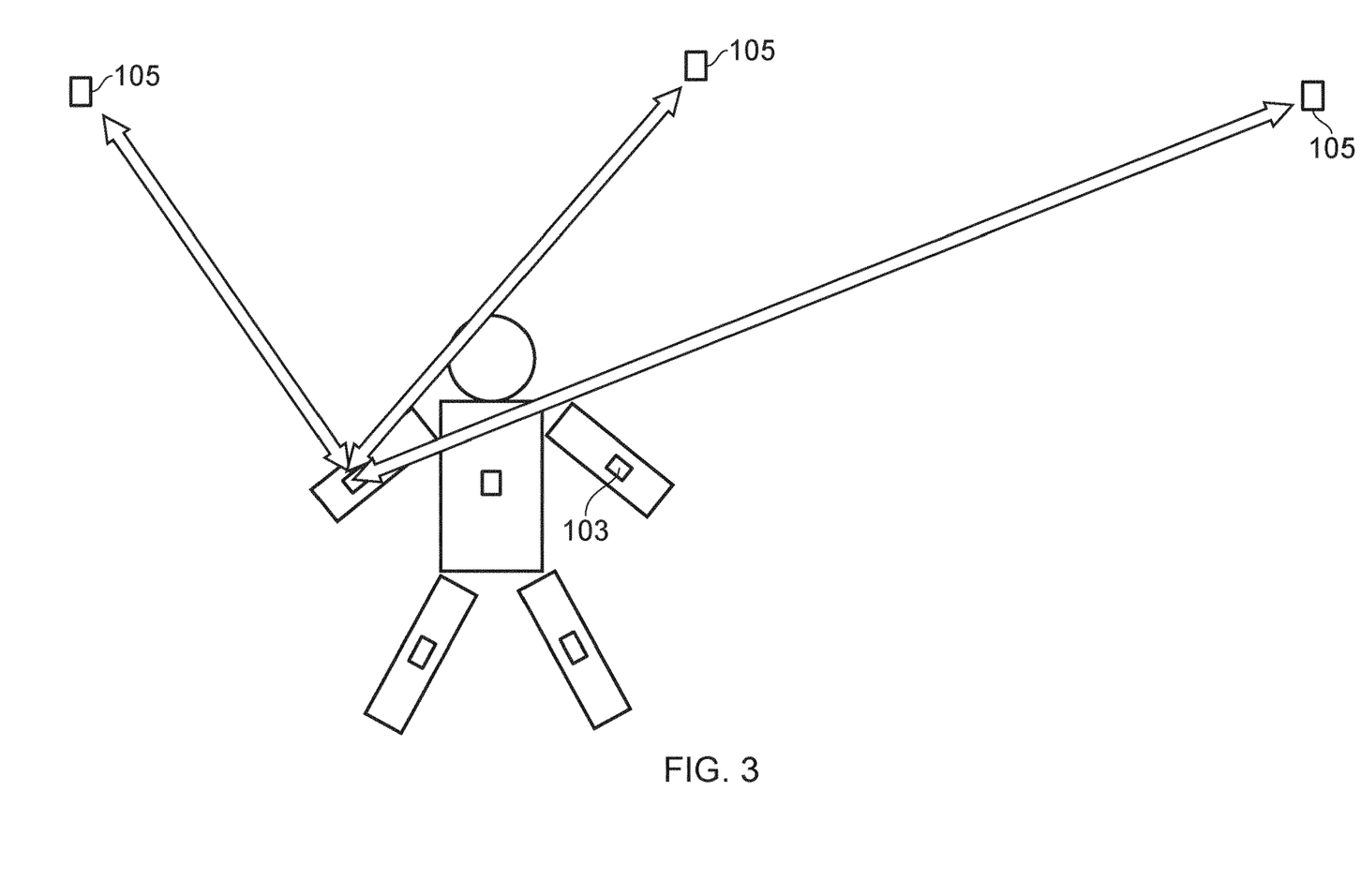
FIG. 3 is a schematic representation of a system according to an example.

FIG. 3 is a schematic representation of a system according to an example, which is similar to that shown in FIG. 2, although the position of the transducers 105 of the second array are depicted in a different location (e.g. ceiling mounted, as opposed to wall mounted in the example of FIG. 2).

Figure 4:
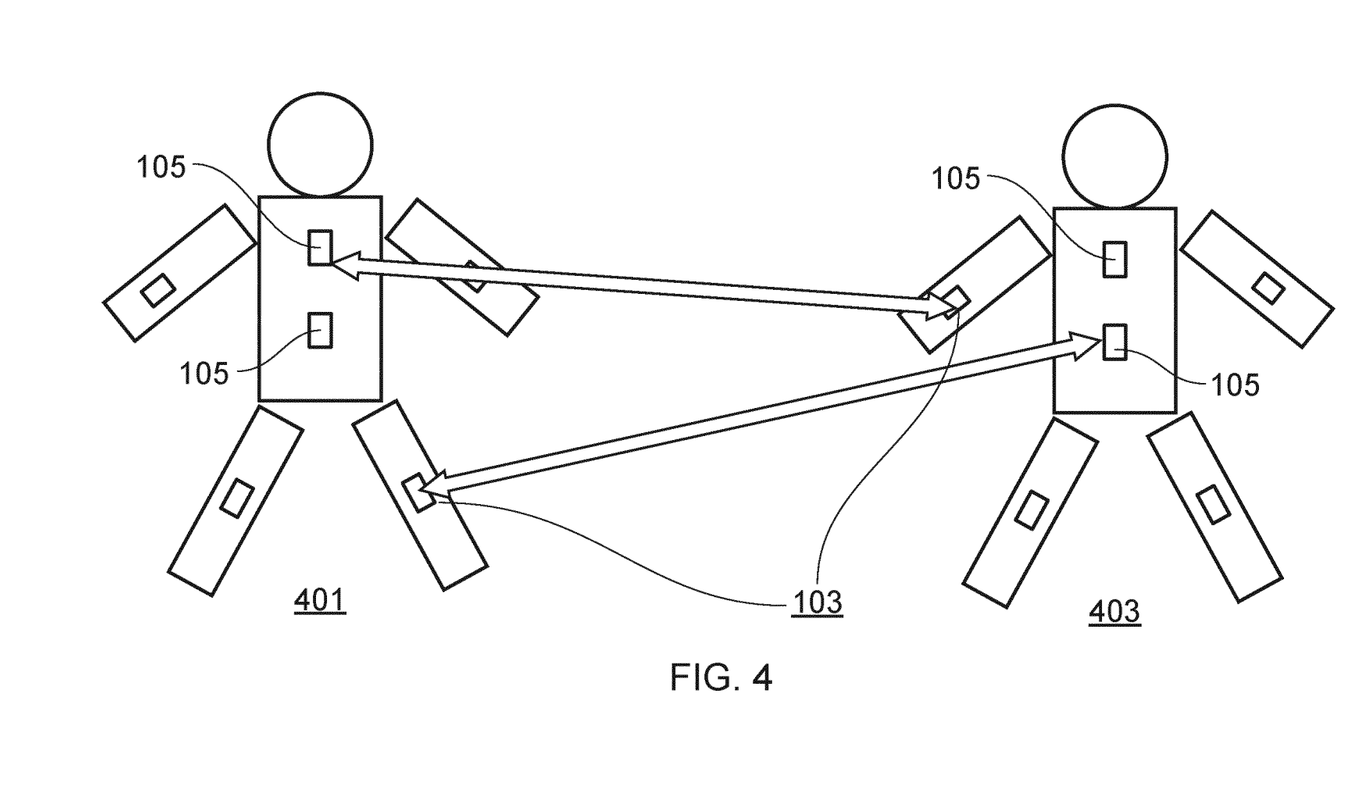
FIG. 4 is a schematic representation of a system according to an example.

FIG. 4 is a schematic representation of a system according to an example. In the example of FIG. 4, multiple users can communicate their moving patterns in real time. One participant (e.g. 401) can take the lead and another one (403) can be the follower enabling real time instruction so as to enable the follower 403 to follow the movements of leader 401. The moving pattern can be shared with more participants thereby enabling multiple followers in real time. As can be seen from FIG. 4, time of flight measurements from transducers of first arrays of users 401, 403 can be determined using transducers of the second arrays that are present on the users 401, 403. That is, time of flight from a transducer of a first array on user 401 is determined by way of reception of a second signal at a transducer 105 of the second user 403, and vice versa. If the position of transducers of the first array are not as expected, i.e. the posture of a user is not as expected, haptic feedback can thus be provided to that user to indicate to them how they should adjust their posture to conform to that expected or desired.

Figure 5:
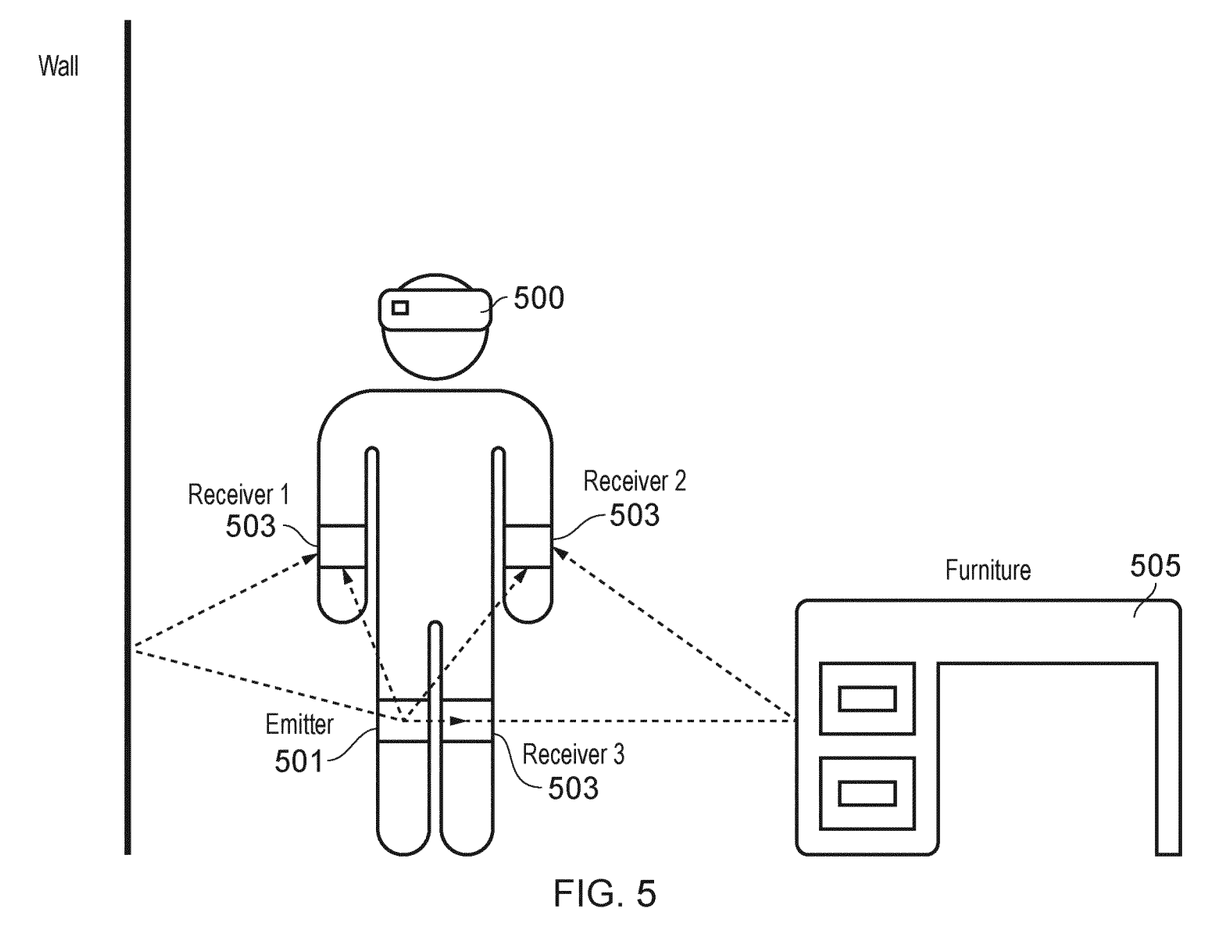
FIG. 5 is a schematic representation of a system according to an example.

FIG. 5 is a schematic representation of a system according to an example. In the example of FIG. 5, information about a user's (500) surrounding environment can be determined. The example of FIG. 5 is described with reference to an indoor environment, although an outdoor implementation is equally possible. A transducer of a first array (which, in the example of FIG. 5 may comprises only transducer) emits ultrasonic pulses as outlined previously, which are transmitted into the surrounding area. The propagation from source 501 to a receiver 503 is multipath, with multiple reflections from objects 505 in the room. The secondary pulses that have been received by the sensors 503 contain information about the locations of these reflective surfaces, which in turn contain information regarding the layout of the room such as the locations of furniture and walls. This could be useful for users with poor eyesight to ensure they do not interfere with obstacles during a performance, for example. It could also be used to inform users of potential obstacles in a VR application with haptics where the user would not be able to see potential hazards, akin to a reverse sensor in a car. This could be applied in VR systems such as a room-scale set-up, where users move around a space as part of the VR experience. The secondary pulse data may also be used to estimate the acoustic reverberation characterisations of the room, which can be communicated to an audio system to optimise a multichannel system, for example.

Thus, in response to a distance determination, a system according to an example can be used to provide haptic feedback to a user using transducers of the first array at the first frequency. In order to initiate haptic feedback, a transducer of the second array can transmit a third signal to a selected piezoelectric transducer of the first piezoelectric transducer array, whereby to cause the said selected piezoelectric transducer of the first piezoelectric transducer array to initiate generation of the first signal at at least one piezoelectric transducer of the first piezoelectric transducer array.

Figure 6:
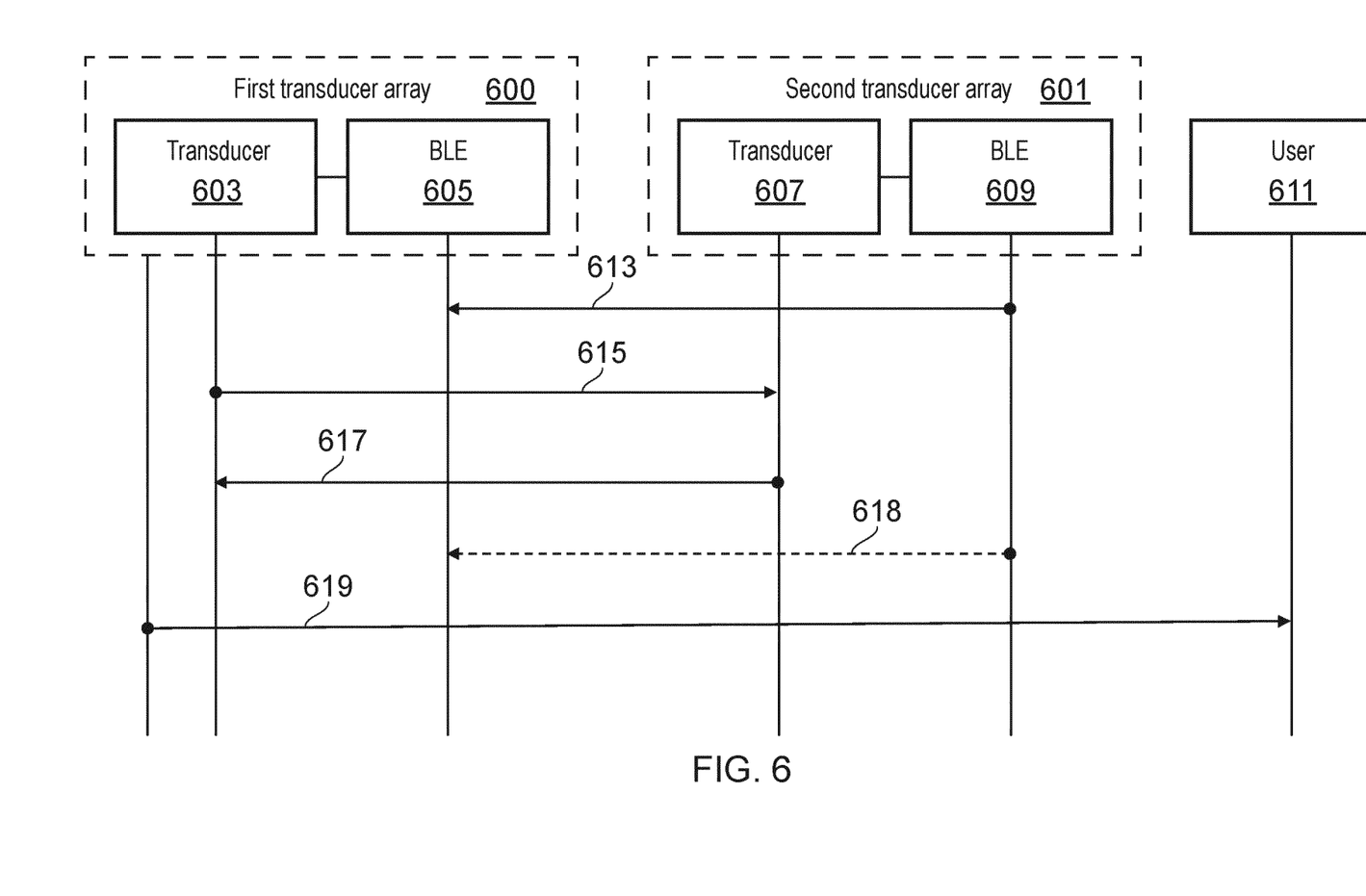
FIG. 6 is a schematic representation of a method according to an example.

FIG. 6 is a schematic representation of a method according to an example. A first transducer array 600 comprises multiple transducers 603, each of which includes a low energy radio frequency module, such as a Bluetooth low energy (or similar) module (BLE) for example, 605. A second transducer array 601 comprises multiple transducers 607, each of which includes a low energy radio frequency module, such as a Bluetooth low energy (or similar) module (BLE) for example, 609. In an example, transducers 603 can generate a first signal at a first frequency, which can be a haptic feedback frequency as described above, and a second signal at a second frequency, which can be an ultrasonic frequency as described above. Transducers 607 can generate a third signal, at the second frequency for example, and can receive a second signal. In the example of FIG. 6, transducer 607 can provide a clock signal 613 using BLE 609, which is received by BLE 605 of transducers 603 in the first array 600 in order to provide a synchronisation for the system. The clock signal 613 may be received by all transducers in the first array 600 by way of their associated BLEs 605.

According to an example, transducer 603 emits a second signal 615 at the second (e.g. ultrasonic) frequency. This may be emitted periodically, such as every 1-100 ms for example. Alternatively, the signal 615 may be emitted in response to a command received at BLE 605 from BLE 609 (i.e. on demand), or a combination of periodically and on-demand. The second signal 615 is received by transducer 607. The second signal 615 includes data representing a time at which the signal was emitted by transducer 603, which time is determined using signal 613. In an example, the second signal 615 further encodes data representing a unique identifier associated with transducer 603.

The time of arrival of signal 615 at transducer 607 can be determined. The time of arrival can be compared to the time of emission in order to determine a time of flight of signal 615. As the speed of the second signal is known, as is the time taken to travel from one transducer to another, the distance between the originating and receiving transducers can be calculated. Multiple such time of flight data, as a result of receipt of signal 615 at multiple ones of the transducers 607 of the second array 601 can therefore be used to determine the position of the transducer 603 using trilateration, multilateration and so on based on the relative distance of an originating transducer from multiple receiving transducers.

In an example, the determined position of the transducer 603 can be compared against an expected or desired position for the transducer 603. For example, if transducer 603 is associated with a particular and predetermined position on a user, such as the wrist for example, the actual position of the transducer 603 and hence the user's wrist can be compared to a desired position therefor. In a similar way, a set of positions relating to multiple transducers in the first array 600 that are disposed on predetermined positions on a user can be used to determine posture and compare instantaneous (or actual) to posture to a desired posture. Thus, for example, if the relative positions of transducers indicates a certain posture that is not a desired posture, a user can be provided with haptic feedback that prompts them to adjust their posture and/or the position of one or more of their arms. legs and so on, as described above.

That is, in response to the comparison, if desired, haptic feedback can be provided to user 611. For example, transducer 607 can emit a third signal 617 at the second frequency. The third signal is received at transducer 603 of the first piezoelectric transducer array 600. In an example, the third signal 617 is configured to cause the said selected piezoelectric transducer 603 of the first piezoelectric transducer array to initiate generation of the first signal 619 at at least one piezoelectric transducer of the first piezoelectric transducer array 600. In an example, the said at least one piezoelectric transducer of the first piezoelectric transducer array 600 can include transducer 603. Thus, at least one piezoelectric transducer of the first piezoelectric transducer array 600 provides a signal 619 for user 611, whereby to provide haptic feedback to the user 611. A transducer that is selected to provide a haptic feedback can be identified using its unique identifier. Thus, in an example, a third signal can encode data representing one or more identifiers of transducers in the first array that are to provide haptic feedback. The third signal can further encode data representing the type of haptic feedback signal to be provided by a transducer, as described above for example.

Alternatively, in another example, BLE 609 can emit a signal 618 received at BLE 605 to initiate generation of the first signal 619 at at least one piezoelectric transducer of the first piezoelectric transducer array 600. That is, the third signal can be provided by BLE 609 and received by BLE 605 for further transmission to other such BLEs of the transducers of the first array 600. In the example of FIG. 6, transducer 603 acts a transducer of the first array 600 configured to initiate generation of the first signal for one or more other transducers of the first array 600.

According to an example, at least one transducer of the first and/or second arrays 600, 601 can further comprise a memory configured to store machine-readable instructions, and a processor configured to execute the said machine-readable instructions. The memory can also store data representing one or more haptic feedback signal profiles.

Figure 7:
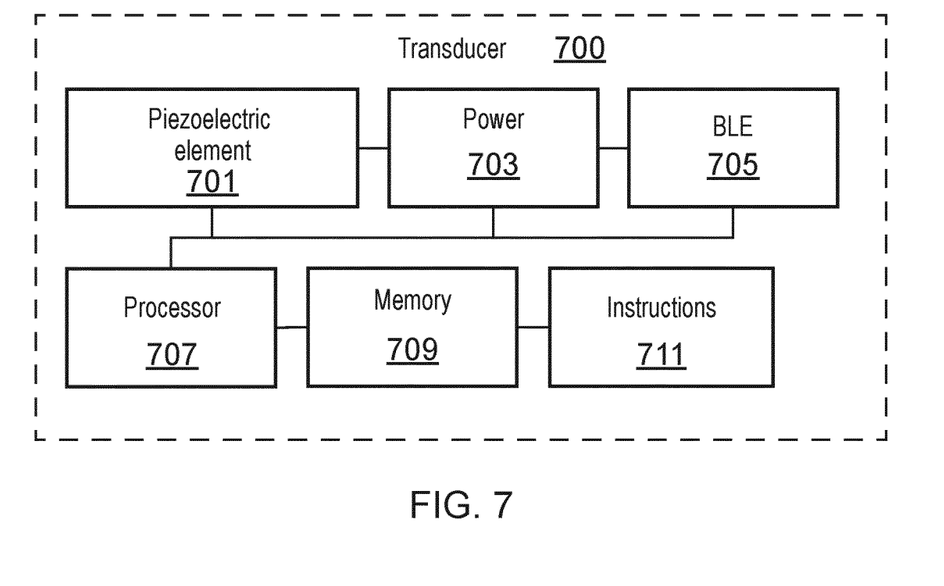
FIG. 7 is a schematic representation of a transducer according to an example.

FIG. 7 is a schematic representation of a transducer according to an example. Transducer 700 can be a transducer of the first and/or second arrays of FIG. 6 for example. A piezoelectric material 701 can be used to generate the first and second signals. For example, application of electric field from power source 703 across the element 701 can cause the element to mechanically deform. Controlling the applied electrical field from source 703 enables the mechanical strain experienced by element 701 to be varied, thus enabling generation of signals at the first or second frequency. Power source 703 can also power BLE 705 and the processor 707 and so on of the transducer 700.

Upon exposure to a signal at the second frequency, element 701 will mechanically stress leading to generation of an electric charge resulting in a detectable voltage across the element 701 that can be detected by a detector (not shown), and which represents a second signal. The detected signal can be decoded by processor 707 to determine, for example, a time stamp and/or identifier, as described above.

Memory 709 can store data representing one or more haptic profiles. For example, a profile can represent a time duration, periodicity, frequency, strength and so on of a haptic feedback signal, with different profiles comprising respective different values for one or more of these signal parameters. Respective haptic feedback profiles can be mapped to desired user movements. For example, as described above, one profile can be used to prompt a user to move an arm up, whilst another can be used to prompt a user to move an arm down, and so on.

Instructions 711 can include instructions to, for example, generate one of the first, second or third signals (either by way of element 701 or BLE 705).

Figure 8:
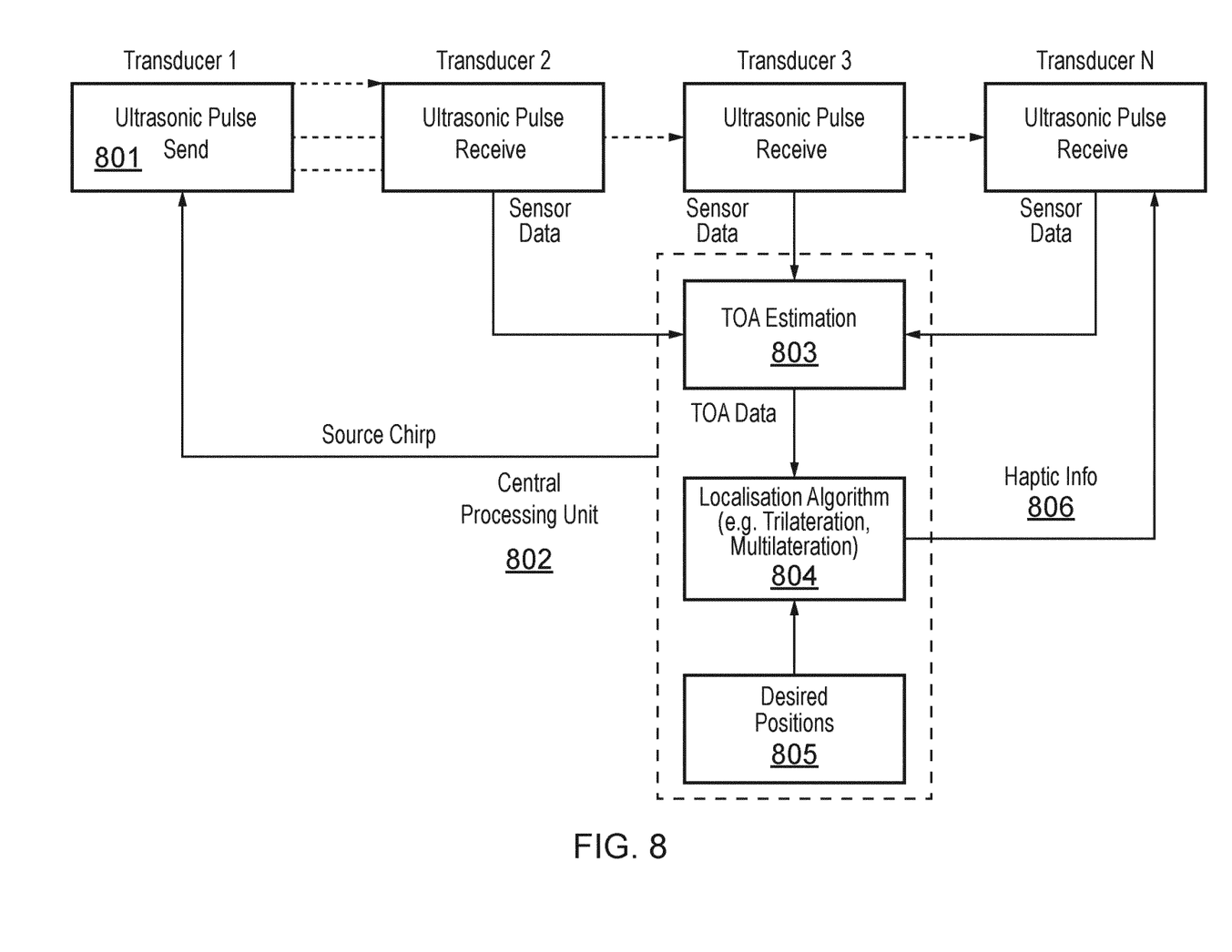
FIG. 8 is a schematic representation of a method according to an example.

FIG. 8 is a schematic representation of a method according to an example. In the example of FIG. 8, N transducers 801 act as both haptic actuators and ultrasonic transceivers, as described above. In the example of FIG. 8, each transducer 801 keeps the same system time via NTP (network time protocol), RF-based clock synchonisation (Bluetooth, WiFi, ZigBee pulses) or are directly wired to a central board such as a microcontroller.

In the illustrated example, one device emits an ultrasonic chirp outside the audible frequency range (above 20 kHz). The other N−1 devices receive this pulse at different times depending on their positions. Note that each device can act as both source and receiver at any given time, and only one device is shown as the source for simplicity. In fact, in an example, the devices could emit pulses simultaneously provided their respective pulses have different carrier frequencies, or operate sequentially if they do not.

The received data at each device is sent to a central processing unit 802, 707 (e.g. microcontroller), either by being wired directly or connected as wireless devices. There may be an ADC at each channel input. By comparing the source waveform with the received data using techniques such as cross-correlation in the ultrasonic band, the TOA 803 can be assessed. This information is then fed into a localisation algorithm 804. For TOA data, lateration-based localisation would be used. The locations of the devices in 3D Cartesian space are now known and could be compared with data of where the transducers should be located 805. Depending on how these locations compare, a haptic signal 806 may be sent to one or more of the devices to communicate a desired response in the user.

The present inventions can be embodied in other specific apparatus and/or methods. The described embodiments are to be considered in all respects as illustrative and not restrictive. In particular, the scope of the invention is indicated by the appended claims rather than by the description and figures herein. All changes that come within the meaning and range of equivalency of the claims are to be embraced within their scope.

The invention claimed is:

1. An apparatus for providing haptic feedback to a user, the apparatus comprising:
a first piezoelectric transducer array comprising multiple first piezoelectric transducers, respective ones of said multiple first piezoelectric transducers being configured to generate a second signal at a second frequency, and at least one of said multiple first piezoelectric transducers being configured to generate a first signal at a first frequency; and
a second piezoelectric transducer array comprising multiple second piezoelectric transducers, respective ones of said multiple second piezoelectric transducers configured to receive the second signal, and at least one of said multiple second piezoelectric transducers configured to:
generate a third signal sent to the respective ones of said multiple first piezoelectric transducers to initiate generation of the first signal at the at least one first piezoelectric transducer of the first piezoelectric transducer array, the first frequency suitable for providing a haptic feedback signal for a user.

2. The apparatus as claimed in claim 1, wherein the third signal is generated at the second frequency.

3. The apparatus as claimed in claim 1, wherein the first piezoelectric transducer array is provided on or as part of an item of clothing.

4. The apparatus as claimed in claim 1, wherein the first frequency is a frequency in the range 10-2000 Hz.

5. The apparatus as claimed in claim 1, wherein the second frequency is a frequency in the range 15-50 kHz.

6. The apparatus as claimed in claim 1, further comprising a control module to receive raw data from respective second piezoelectric transducers of the second piezoelectric transducer array, and, using the raw data, generate position data representing the relative position of the multiple first piezoelectric transducers of the first piezoelectric transducer array.

7. The apparatus as claimed in claim 6, wherein the control module is configured to map the position data to a predetermined haptic response profile, and generate haptic response data representing the haptic response profile.

8. The apparatus as claimed in claim 7, wherein a second piezoelectric transducer of the second piezoelectric transducer array is configured to transmit the haptic response data as part of the third signal.

9. The apparatus as claimed in claim 6, wherein the control module is configured to use respective time stamps from the raw data representing the times of transmission of second signals from respective second piezoelectric transducers of the second piezoelectric transducer array to determine a time of flight of the second signals.

10. The apparatus as claimed in claim 1, further comprising a radio-frequency communication module to receive a data signal from a command transducer of the first piezoelectric transducer array.

11. The apparatus as claimed in claim 10, wherein the module is configured to generate a third signal.

12. The apparatus as claimed in claim 10, wherein the command transducer is configured to transmit data to selected ones of the low energy radio-frequency communication modules of the first piezoelectric transducers of the first piezoelectric transducer array whereby to cause the corresponding first piezoelectric transducers of the first piezoelectric transducer array to generate the first signal.

13. A method, comprising:
emitting ultrasonic signals;
receiving ultrasonic signals;
comparing waveforms of the received and emitted signals;
determining respective times of arrival of the emitting signals; and determining emitting locations;
wherein the emitting comprises emitting a first signal, emitting a second signal, and emitting a third signal, and wherein the frequency of the third signal is equal to the frequency of the second signal;
wherein the third signal is sent to a first piezoelectric transducer of a first piezoelectric transducer array; and
wherein the first signal is generated at a frequency suitable for providing a haptic feedback signal for a user.

14. The method as claimed in claim 13, wherein the frequency of the emitting of the first signal is in the range 10-2000 Hz.

15. The method as claimed in claim 13, wherein the frequency of the emitting of the second signal is in the range 15-50 kHz.

16. The method as claimed in claim 13, further comprising converting the received signals into received data.

17. The method as claimed in claim 16, further comprising converting the received data into position data.

18. The method as claimed in claim 17, comprising converting the position data into haptic response data, and generating a haptic response based on the haptic response data.

19. The method as claimed in claim 13, wherein the emitting of the third signal comprises generating a low energy radio-frequency signal.

\* \* \* \* \*